United States Patent [19]

Hamprecht

[11] Patent Number: 5,283,332

[45] Date of Patent: * Feb. 1, 1994

[54] 2-AMINO(FLUOROALKOXY)PYRIMIDINES AND THE PREPARATION THEREOF

[76] Inventor: Gerhard Hamprecht, 28 Rote-Turm-Strasse, 6940 Weinheim, Fed. Rep. of Germany

[*] Notice: The portion of the term of this patent subsequent to May 25, 2010 has been disclaimed.

[21] Appl. No.: 663,975

[22] Filed: Mar. 4, 1991

[51] Int. Cl.$^5$ .................. C07D 239/42; C07D 239/47
[52] U.S. Cl. ..................................... 544/320
[58] Field of Search ............................ 544/320; 71/92

[56] References Cited

U.S. PATENT DOCUMENTS

| 4,443,243 | 4/1984 | Fory et al. | 71/93 |
| 4,518,776 | 5/1985 | Meyer et al. | 544/320 |
| 4,542,216 | 9/1985 | Pfluger et al. | 544/320 |
| 4,551,531 | 11/1985 | Meyer et al. | 544/320 |
| 4,643,760 | 2/1987 | Meyer et al. | 71/92 |
| 4,831,138 | 5/1989 | Lachhein | 544/320 |

FOREIGN PATENT DOCUMENTS

| 1223591 | 6/1967 | Canada. |
| 70804 | 7/1982 | European Pat. Off.. |
| 0169815 | 1/1986 | European Pat. Off.. |
| 0271833 | 6/1988 | European Pat. Off.. |

OTHER PUBLICATIONS

Chemical Abstracts, vol. 109, entry 88185s (1988).
Rico et al, Tetrahedron Letters, 22 (1981) 323–326.
Pinner, Die Imidoäther und ihre Derivate, published by Oppenheim, Berlin (1892) pp. 2 and 3.
McElvain et al, J.A.C.S., 64 (1942) 1826–1827.
McElvain et al, J.A.C.S. 71 (1949) 40–46.
Redwood et al, Canadian J. of Chemistry, 43, No. 7 (1965) 1893.
Klöter et al, JACS 101 (1979) 347–349.
Proceedings of the Academy of Sciences of the USSR, vol. 133, Nos. 1–6 Jul.–Aug. 1960.
The Journal of the American Chemical Society, vol. LXXXIII, 1961, Oct.–Dec. pp. 4860–4861.
Chemical Abstracts, vol. 99, (1983) entry-53396, Stammann et al.
Chemical Abstracts, vol. 105, 115325, Tramor (1986).
Chemical Abstracts, vol. 107, 1987, 96978, Withers et al.

Primary Examiner—John M. Ford
Attorney, Agent, or Firm—Keil & Weinkauf

[57] ABSTRACT

2-Amino-(fluoroalkoxy)pyrimidines of the formula I

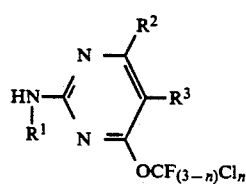

where
R$^1$ is hydrogen, alkyl, alkenyl or alkynyl,
R$^2$ is hydrogen, halogen or haloalkyl, or else trifluoromethoxy or chlorodifluoromethoxy,
R$^3$ is hydrogen, halogen or C$_1$–C$_4$-haloalkyl and
n is 0 or 1, are prepared as described.

7 Claims, No Drawings

2-AMINO(FLUOROALKOXY)PYRIMIDINES AND THE PREPARATION THEREOF

The present invention relates to novel 2-amino(-fluoroalkoxy)pyrimidines of the formula I

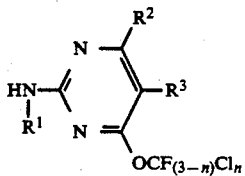

where
$R^1$ is hydrogen, $C_1$–$C_4$-alkyl, $C_3$–$C_4$-alkenyl or $C_3$–$C_4$-alkynyl,
$R^2$ is hydrogen, halogen or $C_1$–$C_4$-haloalkyl, or else trifluoromethoxy or chlorodifluoromethoxy,
$R^3$ is hydrogen, halogen or $C_1$–$C_4$-haloalkyl and n is 0 or 1.

The present invention also relates to a process for preparing the pyrimidines I by reacting fluoroalkoxy-2-halopyrimidines with amines.

The pyrimidines I are valuable intermediates for organic syntheses, especially for preparing crop protection agents.

There are many indications in the literature that, because of similar electronic properties, fluoroalkyl and fluoroalkoxy groups are equivalent to halogens. Measurements of pKa (Proc. Nat. Acad. Sci. USA 134 (1960) 1207, J. Am. Chem. Soc. 83 (1961) 4860) demonstrate that, for example, fluoroalkoxy groups are inductive electron attractors but, conversely, also act as electron donors because of the possibility of resonance. Taking all the effects into account, the trifluoromethoxy group is in fact more strongly deactivating than the halogens, so that the term "superhalogens" has been used (J. Am. Chem. Soc. 83 (1961) 4860). This applies in the same way to their replaceability by nucleophiles. For example, Chemical Abstracts 87, 53396 demonstrates that two haloalkyl groups in 2,4-bis (trichloromethyl) -6-trifluoromethyl-s-triazine are replaced on stirring with basic amines in benzene. The ability of trifluoromethoxy to act as leaving group is also used, for example, in sugar chemistry (CA. 105, 115325; 107, 96978).

Thus, with this background, the existing processes for preparing 2-amino(fluoroalkoxy)pyrimidines are very elaborate and timeconsuming. For example, it is necessary first to convert an appropriately substituted 2-halopyrimidine with methyl mercaptan, which is toxic, into the 2-methylthiopyrimidine, which is then oxidized to the 2-methylsulfonyl derivative which is subjected to nucleophilic displacement with an amine (U.S. Pat. No. 4,542,216).

We have found that the novel 2-amino(fluoroalkoxy)pyrimidines of the formula I

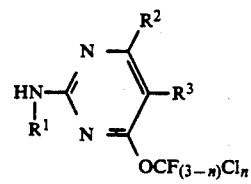

where $R^1$, $R^2$, $R^3$ and n have the abovementioned meanings, are obtained advantageously by reacting 2-halopyrimidines of the formula II

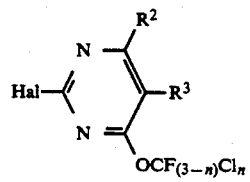

where Hal is fluorine, chlorine, bromine or iodine, and $R^2$, $R^3$ and n have the abovementioned meanings, with an amine of the formula III

H—NH—$R^1$     III where $R^1$ has the abovementioned meaning.

The reaction of 2,4-difluoro-6-trifluoromethoxypyrimidine and ammonia is shown in the following diagram:

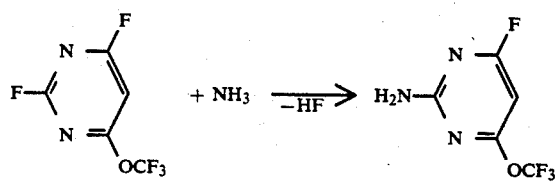

The process provides novel 2-amino(fluoroalkoxy)-pyrimidines in high yields and purity in a straightforward and economic manner. Against expectation, fluoroalkoxy groups are not replaced under the reaction conditions. In view of the prior art, all these advantageous properties are surprising.

Preferred final products I and, accordingly, preferred starting materials II are those in whose formulae $R^1$ is hydrogen, $C_1$–$C_4$-alkyl such as methyl, ethyl, n-propyl, i-propyl, n-butyl, sec.-butyl, i-butyl or tert.-butyl, $C_3$–$C_4$-alkenyl such as 2-propenyl, 2-methylethenyl, 2-butenyl, 3-butenyl, 1-methyl-2-propenyl or 2-methyl-2-propenyl, $C_3$–$C_4$-alkynyl such as propargyl, 2-butynyl, 3-butynyl or 1-methyl-2-propynyl, $R^2$ and $R^3$ are, independently of one another, hydrogen, fluorine, chlorine, bromine, trichloromethyl, dichlorofluoromethyl, chlorodifluoromethyl, trifluoromethyl, 1,1-dichloro-2,2,2-trifluoroethyl, 1,1,2,2,2-pentafluoroethyl or 1,1,2,2,2-pentachloroethyl, and, furthermore, $R^2$ is trifluoromethoxy or chlorodifluoromethoxy, and n is 0 or 1.

Among the amines which can be employed, the following may be mentioned: ammonia, methylamine, ethylamine, n-propylamine, isopropylamine, n-butylamine, isobutylamine, sec.-butylamine, tert.-butylamine, 2-propenylamine, 2-methylethenylamine, 2-butenylamine, 3-butenylamine, 1-methyl-2-propenylamine, 2- methyl-2-propenylamine, propargylamine, 2-butynylamine, 3-butynylamine and 1-methyl-2-propynylamine.

The 2-halopyrimidines II can be reacted with the amines III in an aprotic polar solvent at from $-80°$ to $40°$ C., either employing the amine III in excess relative to II or using an additional organic base.

The reaction of the 2-halopyrimidine II with the amine III can be carried out in the absence or, advantageously, in the presence of a solvent. Particularly suitable solvents are the following:

Ethers such as methyl tert.-butyl ether, diethyl ether, ethyl propyl ether, n-butyl ethyl ether, di-n-butyl ether, diisobutyl ether, diisoamyl ether, diisopropyl ether, cyclohexyl methyl ether, tetrahydrofuran, 1,2-dimethoxyethane, diethylene glycol dimethyl ether and anisole, esters such as ethyl acetate, n-butyl acetate and isobutyl acetate, and chlorohydrocarbons such as methylene chloride, 1,1,2,2-tetrachloroethane, 1,1-dichloroethylene, 1,2-dichloroethane, chlorobenzene, 1,2-dichlorobenzene and 1-chloronaphthalene, and mixtures of these solvents.

The solvent is expediently used in an amount of from 100 to 2000% by weight, preferably 400 to 1200% by weight, based on the starting material II.

It is advantageous to add from 1.8 to 2.5, in particular 1.95 to 2.2, mole equivalents of the amine III based on the starting material II over the course of 0.5 to 2 hours to the starting material II in one of the abovementioned solvents at from $-80°$ to $40°$ C., preferably $-70°$ to $25°$ C., to stir until the reaction is complete (after about 3 hours) and then to allow to warm to $25°$ C. for the working up.

If only approximately the stoichiometric amount of the amine III is employed, it is expedient to use an additional organic base in order to trap the hydrogen halide which is generated. Suitable for this are the customary organic bases such as trimethylamine, triethylamine, ethyldiisopropylamine, triisopropylamine, N,N-dimethylaniline, N,N-dimethylcyclohexylamine, N-methylpyrrolidine, pyridine, quinoline, $\alpha$-, $\beta$- or $\gamma$-picoline, 2,4- or 2,6-lutidine and triethylenediamine. It generally suffices to add from 0.9 to 1.1 equivalents of the base relative to starting material II.

The reaction can be carried out under atmospheric or superatmospheric pressure, continuously or batchwise.

The working up can be carried out in a conventional manner, eg. the reaction mixture is extracted with water to remove the salts, and the organic phase is dried and purified, eg. by chromatography. However, it is also possible to concentrate the organic phase directly and to stir the residue with a solvent.

With a view to the further processing thereof to herbicidal compounds, eg. sulfonylurea derivatives, the following pyrimidines of the formula I are particularly preferred:
2-amino-4-chloro-6-trifluoromethoxypyrimidine,
2-amino-4-fluoro-6-trifluoromethoxypyrimidine,
2-amino-4-chloro-6-chlorodifluoromethoxypyrimidine,
2-amino-4-fluoro-6-chlorodifluoromethoxypyrimidine,
2-amino-4,6-bis(trifluoromethoxy)pyrimidine,
2-amino-4,6-bis(chlorodifluoromethoxy)pyrimidine,
2-amino-4-trifluoromethoxy-6-trifluoromethylpyrimidine,
2-amino-4-chlorodifluoromethoxy-6-trifluoromethylpyrimidine,
2-amino-4,5-dichloro-6-trifluoromethoxypyrimidine,
2-amino-4-chloro-6-trifluoromethoxy-5-trifluoromethylpyrimidine,
2-methylamino-4-chloro-6-trifluoromethoxypyrimidine,
2-methylamino-4-fluoro-6-trifluoromethoxypyrimidine,
2-methylamino-4-chloro-6-chlorodifluoromethoxypyrimidine,
2-methylamino-4-fluoro-6-chlorodifluoromethoxypyrimidine,
2-methylamino-4,6-bis(trifluoromethoxy)pyrimidine,
2-methylamino-4,6-bis(chlorodifluoromethoxy)pyrimidine,
2-methylamino-4-trifluoromethoxy-6-trifluoromethylpyrimidine,
2-methylamino-4-chlorodifluoromethoxy-6-trifluoromethylpyrimidine,
2-methylamino-4,5-dichloro-6-trifluoromethoxypyrimidine,
2-methylamino-4-chloro-6-trifluoromethoxy-5-trifluoromethylpyrimidine,
2-allylamino-4-chloro-6-trifluoromethoxypyrimidine,
2-allylamino-4-fluoro-6-trifluoromethoxypyrimidine,
2-allylamino-4-chloro-6-chlorodifluoromethoxypyrimidine,
2-allylamino-4-fluoro-6-chlorodifluoromethoxypyrimidine,
2-allylamino-4,6-bis(trifluoromethoxy)pyrimidine,
2-allylamino-4,6-bis(chlorodifluoromethoxy)pyrimidine,
2-allylamino-4-trifluoromethoxy-6-trifluoromethylpyrimidine,
2-allylamino-4-chlorodifluoromethoxy-6-trifluoromethylpyrimidine,
2-allylamino-4,5-dichloro-6-trifluoromethoxypyrimidine,
2-allylamino-4-chloro-6-trifluoromethoxy-5-trifluoromethylpyrimidine.

The 2-halopyrimidines required as starting materials II are prepared by the process described in German Application P 40 07 317 3 which corresponds to U.S. Ser. No. 663,342, filed Mar. 4, 1991, which is depicted in the following reaction scheme:

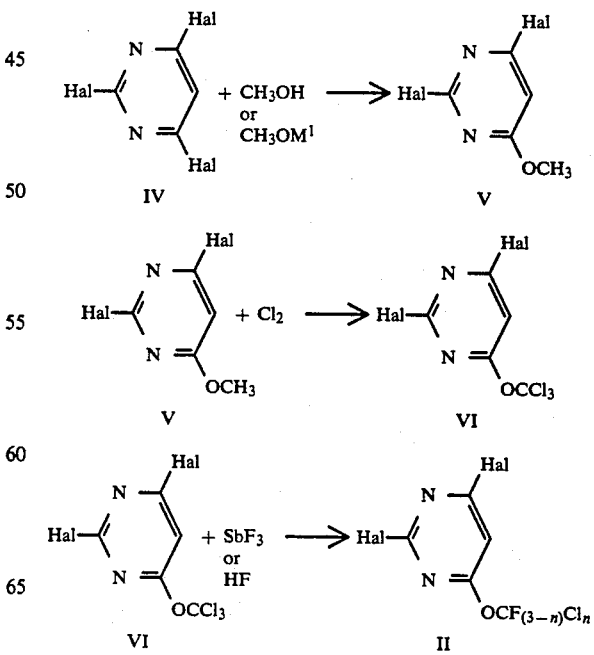

Thus, for example, a 2,4,6-trihalopyrimidine IV can be reacted in an aprotic polar solvent
a) with methanol in the presence or absence of a base or
b) with a methanolate where $M^1$ is the cation of an alkali metal such as lithium, sodium or potassium or the equivalent of an alkaline earth metal such as the magnesium, calcium or barium cation, in the presence of methanol, at from −40° to 120° C. to give the methoxypyrimidine. These reactions can be carried out under atmospheric or superatmospheric pressure (from 1 to 10 bar, preferably 1 to 5 bar), continuously or batchwise.

Hal in the reaction scheme is fluorine, chlorine or bromine.

The following solvents are suitable for reacting the trihalopyrimidine with methanol:

Ethers such as methyl tert.-butyl ether, diethyl ether, ethyl propyl ether, n-butyl ethyl ether, di-n-butyl ether, diisobutyl ether, diisoamyl ether, diisopropyl ether, cyclohexyl methyl ether, tetrahydrofuran, 1,2-dimethoxyethane, diethylene glycol dimethyl ether and anisole, chlorohydrocarbons such as 1,1,2,2-tetrachloroethane, 1,1-dichloroethylene, chlorobenzene, 1,2-dichlorobenzene and 1-chloronaphthalene, and mixtures thereof.

The solvent is expediently used in an amount of from 100 to 2000% by weight, preferably 500 to 1500% by weight, based on the starting material.

However, the reaction of the starting materials IV is expediently carried out directly in excess methanol as solvent. It is possible to add an alkali metal methanolate in an equivalent amount or in an amount which is up to 5 mol % above or below this, based on the starting material, to a suspension of the starting material in from 5 to 20 times the amount by weight of methanol as solvent, based on the starting material IV, over the course of up to one hour at from about −20 to 80° C. To complete the reaction, the mixture is then stirred at from 0° to 120° C., preferably 0° to 100° C., for about ½ to 8 hours.

The methoxypyrimidines are isolated by conventional working up methods.

The methoxypyrimidine is chlorinated to give the trichloromethoxypyrimidine at, for example, from 60° to 1800° C.

Suitable chlorinating agents are elemental chlorine and substances which release chlorine such as sulfuryl chloride or phosphorus pentachloride. It is also possible to generate chlorine in situ by oxidizing hydrochloric acid, for example with pyrolusite or by anodic chlorination.

The chlorination can be carried out in the presence of an inert solvent, for example a chlorohydrocarbon such as chloroform, tetrachloromethane, chlorobenzene, 1,2- or 1,3- or 1,4-dichlorobenzene, a nitrile such as acetonitrile or propionitrile, a nitro compound such as nitrobenzene, a carboxylic acid such as acetic or propionic acid, an anhydride such as acetic anhydride, an acid chloride such as chloroacetyl chloride, α-chloropropionyl chloride or α,α-dichloropropionyl chloride, an inorganic acid halide such as phosphorus trichloride or phosphorus oxychloride or, preferably, without solvent in the melt of the starting material.

A radical initiator can be used to increase the reaction rate; suitable for this is irradiation with light, preferably UV light, or addition of α,α'-azoisobutyronitrile, expediently in an amount of from 0.2 to 7 mol % based on the starting material. The reaction rate can also be increased by addition of a catalyst; suitable for this is phosphorus pentachloride, expediently in an amount of from 0.5 to 7 mol % based on the starting material V. In this case, the starting material V is mixed with the catalyst and then the chlorination is started. In place of phosphorus pentachloride, it is also possible to add components which form it under the reaction conditions, eg. phosphorus trichloride or yellow phosphorus, and then to start with the chlorination.

starting material V can be reacted with chlorine in approximately stoichiometric amount or, preferably, in excess, advantageously with from 3.1 to 11, in particular 3.3 to 5, moles of chlorine per methoxy equivalent in the starting material V. The reaction can be carried out at from 60° to 180° C., advantageously from 100° to 150° C., under atmospheric or superatmospheric pressure, continuously or batchwise.

when chlorination is carried out under 1 bar it is expedient to employ from 3.3 to 5 moles of chlorine gas based on one methoxy equivalent in the starting material V, which corresponds to a chlorine conversion of from 91 to 60%. It is possible, by suitable measures, eg. by use of moderate superatmospheric pressure, expediently from 1 to 10 bar, or by use of a bubble column, to increase the chlorine conversion. It is advantageous to maximize the time during which the chlorine gas is in contact with the organic phase by, for example, vigorously stirring the latter or forcing the chlorine gas to pass through a thick layer of the organic phase.

The reaction time is generally from about 0.5 to 12 hours.

The procedure in a preferred embodiment of the process is to pass the required amount of chlorine gas over the course of from 0.5 to 12 hours, preferably 1 to 10 hours, into the vigorously stirred liquid starting material V, starting at from 60° to 80° C. and increasing the temperature continuously, possibly by utilizing the exothermic nature of the reaction, to from 100° to 150° C. at the end of the reaction. In the case of large batches, the exothermic nature of the reaction must be taken into account by applying external cooling or by suitable metering in of the chlorine; when the reaction subsides the cooling bath is removed and the mixture may then be heated further if necessary.

The final products are worked up and isolated in a conventional manner. For example, residual hydrogen chloride, chlorine or catalyst can be driven out of the hot organic phase using an inert gas; this results in a high yield of a reasonably pure crude product. It can be further purified by distillation or chromatography or else employed immediately for further reactions.

The reaction of the trichloromethoxypyrimidine VI with a fluorinating agent is carried out at from 0° to 170° C., for example.

Suitable fluorinating agents are antimony trifluoride in the presence or absence of catalytic amounts of an antimony(V) salt, eg. antimony(V) chloride, and hydrogen fluoride.

it is expedient to use an excess of from 1 to 200, preferably 5 to 20, mol % of antimony trifluoride per trichloromethyl equivalent. The amount of antimony(V) salt catalyst is from 1 to 20, preferably 5 to 18, mol % per trichloromethyl equivalent. The starting material VI is preferably metered at from 90° to 130° C. into the mixture containing the fluorinating agent, which is then heated at from 140° to 170° C. for from 10 to about 120 minutes. Working up is then carried out by distillation.

However, the reaction can also be carried out continuously by adding the starting material VI at from 140° to 170° C. over the course of from 10 to about 120 minutes and simultaneously distilling out under reduced pressure the lower boiling final product II. Traces of antimony salts which have been carried over can be removed by extraction with concentrated hydrochloric acid.

Halogen replacement can be stopped at the chlorodifluoromethoxy stage by using only small amounts, eg. from 0.2 to 1 mol %, of antimony(V) salt catalyst, or none at all, and reducing the amount of antimony trifluoride to from 60 to 90 mol % per trichloromethyl equivalent.

In place of antimony trifluoride it is possible to use hydrogen fluoride at from 0 to 170° C., preferably 40° to 120° C. This is carried out by mixing the starting material VI with an excess of from 300 to 700, preferably 350 to 400, mol % of hydrogen fluoride per trichloromethyl equivalent in an autoclave and stirring for from 10 minutes to about 10 hours. In general, the reaction is complete after about 4 hours. After the pressure has been released and volatiles have been removed, working up is carried out as described.

The novel 2-amino(fluoroalkoxy)pyrimidines I are valuable intermediates for preparing crop protection agents. They can be converted by the process of German Patent Application P 40 07 683 0 (O.Z. 0050/41452) of the same date by reacting, for example, 2-amino-4-fluoro-6-trifluoromethoxypyrimidine with methanol into the corresponding 2-amino-6-methoxy-4-trifluoromethoxypyrimidine which reacts with 2-carbomethoxybenzenesulfonyl isocyanate to give herbicidal sulfonylureas. However, they can also be reacted directly with the said isocyanate to give herbicidal sulfonylureas.

EXAMPLES

I EXAMPLES FOR THE PREPARATION OF THE PRECURSORS (cf. German Application P 40 07 317 3 (O.Z. 0050/41450) of the same date)

Example I.1

2-Chloro-4-trichloromethoxy-6-trichloromethylpyrimidine a) 2-Chloro-4-methoxy-6-trichloromethylpyrimidine 293.1 g (1.692 mol) of 30% strength sodium methylate solution were added over the course of 1½ hours to a stirred solution of 434 g (1.692 mol) of 2,6-dichloro-4-trichloromethylpyrimidine in 1 l of 1,2-dichloroethane at 0° to 5° C. The mixture was then stirred at 0° to 5° C. for 1 hour and at 25° C. for 12 hours and then extracted with water and with saturated brine. Drying over magnesium sulfate and concentration resulted in 423 g (95% of theory) of the title compound as an almost colorless oil.

$^1$H-NMR (CDCl$_3$) (ppm) OCH$_3$ (s/3H) 4.1; CH (s/1H) 7.25.

b)
2-Chloro-4-trichloromethoxy-6-trichloromethylpyrimidine

Chlorine was passed into a mixture of 210 g (0.802 mol) of a) and 260 mg (0.0016 mol) of α,α'-azoisobutyronitrile, initially at 110° C., with uv irradiation and monitoring of the progress of the reaction by gas chromatography. The temperature stabilized at 140° C. even after removal of the heating bath. After the reaction had subsided a total of 341 g (4.8 mol) of chlorine was passed in at 120° C. over the course of 5½ hours. The reaction mixture was cooled to 40° C. and 70 ml of n-pentane were stirred in. The precipitate was filtered off with suction, washed with petroleum ether and dried, resulting in 163 g (55% of theory) of the title compound of melting point 67°-69° C.

The gas chromatogram of the filtrate (113.8 g) showed that it was composed of 83% title compound, 4% 2-chloro-4-dichloromethoxy-6-trichloromethylpyrimidine and 9% 2,4-dichloro-6-trichloromethylpyrimidine. The total yield of the title compound was 87.6% of theory.

Example I.2

2,4-Difluoro-6-trichloromethoxypyrimidine a) 2,4-Difluoro-6-methoxypyrimidine (Preparation by the process of the older German Patent Application P 39 00 471.6)

335.8 g (1.865 mol) of 30% strength sodium methylate (in methanol) were added to a mixture of 250 g (1.865 mol) of 2,4,6-trifluoropyrimidine and 1.4 l of methanol at −20° C. over the course of 45 minutes, and the mixture was stirred at this temperature for a further 30 minutes. It was then allowed to warm to 25° C. and concentrated to about 1/5 of its volume.

The resulting mixture was partitioned between diethyl ether and water, and then the organic phase was dried over magnesium sulfate and concentrated. Distillation (1.1 m column, 3 mm V-shaped packing) resulted in 141.6 g (52% of theory) of the title compound of boiling point 144°-145° C.

Distillation of the residue with a Normag head resulted in 114.4 g (42% of theory) of 4,6-difluoro-2-methoxypyrimidine of boiling point 157°-161° C.

b) 2,4-Difluoro-6-trichloromethoxypyrimidine 210 g (2.96 mol) of chlorine were passed over the course of 2½ hours into 123 g (0.843 mol) of 2,4-difluoro-6-methoxypyrimidine which was stirred at 130° C. and exposed to UV irradiation, with monitoring of the progress of the reaction by gas chromatography. The reaction mixture was distilled through a 10 cm Vigreux column under reduced pressure, resulting in 190.2 g (90.5% of theory) of the title compound of boiling point 40°-43° C./0.2 mbar.

Example I.3

2,4-Dichloro-6-trichloromethoxypyrimidine 303 g (4.27 mol) of chlorine were passed into a mixture of 209 g (1.168 mol) of 2,6-dichloro-4-methoxypyrimidine and 2 g (0.012 mol) of α,α'-azoisobutyronitrile while stirring at 80° C. for ½ hour, at 100° C. for 1 hour, at 120° C. for 3 hours and at 150° C. for 3 hours and subjecting to UV irradiation, with monitoring of the progress of the reaction by gas chromatography. The reaction mixture was then distilled through a 50 cm column containing 4 mm stainless steel Raschig rings under reduced pressure. 241.3 g (73% of theory) of the title compound of boiling point 87°-88° C./0.4 mbar, melting point 55°-56° C. were obtained.

Example I.4

2,4-Difluoro-6-trifluoromethoxypyrimidine 49.9 g (0.2 mol) of 2,4-difluoro-6-trichloromethoxypyrimidine were added over the course of 15 minutes to a stirred mixture of 39.3 g (0.22 mol) of antimony trifluoride and 9.38 g (0.031 mol) of antimony pentachloride at 100° C. The bath temperature was increased from 100° to 150° C. over the course of 25 minutes, and the mixture was then stirred for 30 minutes, reflux taking place at from 120° to 125° C. Subsequent distillation resulted in 37.1 g (92.7% of theory) of the title compound of boiling point 125°-127° C.

Example I.5

6-Chlorodifluoromethoxy-2,4-difluoropyrimidine 93 g (0.373 mol) of 2,4-difluoro-6-trichloromethoxypyrimidine were added over the course of 10 minutes to a stirred mixture of 44.5 g (0.249 mol) of antimony trifluoride and 0.94 g (0.0031 mol) of antimony pentachloride at 100° C. The bath temperature was raised from 100° to 175° C. over the course of 25 minutes, reflux taking place at 145° C. After stirring for 1½ hours, the reaction product was distilled out at 146°-150° C. The distillate was dissolved in 200 ml of methylene chloride, and the solution was extracted with 6 N hydrochloric acid and dried over magnesium sulfate. Concentration under reduced pressure resulted in a residue of the title compound in a yield of 63.7 g = 78.8% of theory.

Example I.6

2-Fluoro-4-trifluoromethoxy-6-trifluoromethylpyrimidine 80 g (0.219 mol) of 2-chloro-4-trichloromethyl-6-trichloromethoxypyrimidine were added over the course of 5 minutes to a stirred mixture of 93.9 g (0.525 mol) of antimony trifluoride and 18.7 g (0.0627 mol) of antimony pentachloride at 100°. The bath temperature was raised to 140° C. over the course of 10 minutes, and the mixture was then stirred for 1 hour, during which it refluxed vigorously. The reaction product was distilled at 135°-140° C. and, towards the end, at 95° C./50 mbar. The distillate was taken up in methylene chloride, and the solution was extracted with 6 N hydrochloric acid and dried over magnesium sulfate. Concentration under reduced pressure resulted in the title compound in a yield of 35.9 g (65.5% of theory).

Example I.7

2,4-Dichloro-6-trifluoromethoxypyrimidine 115 g (0.407 mol) of 2,4-dichloro-6-trichloromethoxypyrimidine were added over the course of 5 minutes to a stirred mixture of 80 g (0.447 mol) of antimony trifluoride and 18.77 g (0.0627 mol) of antimony pentachloride at 100° C., during which the reaction temperature rose to 140° C. The mixture was then stirred at 150° C. for 45 minutes. The title compound distilled at 128° C. under 210 mbar; remaining volatiles were driven over at 110° C./22 mbar. The distillate was dissolved in methylene chloride, and the solution was extracted with 6 N hydrochloric acid and dried over magnesium sulfate. Concentration under reduced pressure resulted in the title compound in a yield of 80 g (84.4% of theory) of colorless oil of $n_D^{25}=1.4604$.

II PREPARATION OF COMPOUNDS I ACCORDING TO THE INVENTION

Example II.1

2-Amino-4-chlorodifluoromethoxy-6-fluoropyrimidine 9.8 g (0.578 mol) of gaseous ammonia were passed over the course of one hour into a stirred mixture of 62.5 g (0.289 mol) of 2,4-difluoro-6-chlorodifluoromethoxypyrimidine and 300 ml of tetrahydrofuran at −75° to −70° C. The mixture was stirred at −70° C. for one hour and then warmed to room temperature. The precipitate was filtered off with suction and partitioned between ethyl acetate and water, and the organic phase was dried over magnesium sulfate, filtered and concentrated. The residue was dissolved in ethyl acetate, chromatographed on silica gel with 5:1 petroleum ether/ether and concentrated. 46.5 g (75.3% of theory) of the title compound were obtained as colorless crystals of melting point 77°-80° C.

Example II.2

2-Amino-4-fluoro-6-trifluoromethoxypyrimidine 8.7 g (0.51 mol) of gaseous ammonia were passed over the course of 1 hour into a stirred mixture of 51 g (0.255 mol) of 2,4-difluoro-6-trifluoromethoxypyrimidine and 200 ml of diethyl ether at −75° to −70° C. The mixture was stirred at −70° C. for 1½ hours and at room temperature for 1 hour and then concentrated under reduced pressure. The residue was taken up in methylene chloride and the organic phase was extracted with water, dried, concentrated and chromatographed on silica gel with 8:1 petroleum ether/ether, resulting in 38.1 9 (75.6% of theory) of the title compound as colorless crystals of melting point 86°-89° C.

Example II.3

2-Amino-4-chloro-6-trifluoromethoxypyrimidine 4.3 g (0.25 mol) of gaseous ammonia were passed over the course of 45 minutes into a stirred mixture of 23.3 g (0.1 mol) of 2,4-dichloro-6-trifluoromethoxypyrimidine and 150 ml of methyl tert.-butyl ether at −50° to −45° C. The mixture was stirred at −50° C. for 30 minutes, at −30° C. for 1 hour and at 25° C. for 1 hour. The precipitate was filtered off with suction, washed with water and dried, resulting in 5.4 g (33.1% of theory) of 4-amino-2,4-dichloropyrimidine of melting point 270°-272° C. as by-product. The filtrate was washed with water, dried and concentrated under reduced pressure, and the residue was chromatographed with 5:1 petroleum ether/ether, the initial fractions yielding 3 g (12.8% of theory) of starting material as a colorless oil, and subsequent fractions containing 9 g (42% of theory) of the title compound as colorless crystals of melting point 55°-56° C. Conversion was 48.3%.

Example II.4

4-Chlorodifluoromethoxy-6-fluoro-2-methylaminopyrimidine 20.3 g (0.0938 mol) of 4-chlorodifluoromethoxy-2,6-difluoropyrimidine were introduced into 150 ml of tetrahydrofuran and, while stirring at −70° to −60° C., 5.8 g (0.188 mol) of gaseous methylamine were added over the course of 30 minutes. The mixture was stirred for 1 hour each at −70° C., 0° C. and 25° C. and concentrated under reduced pressure. The residue was stirred with water, the mixture was extracted with ethyl acetate, and the extract was dried over magnesium sulfate. The residue from concentration under reduced pressure was chromatographed on silica gel with 5:1 petroleum ether/ether. The first fractions contained the title compound of melting point 57°-61° C. in a yield of 12.5 g (58.5%).

Example II.5

2-Amino-4-trifluoromethoxy-6-trifluoromethylpyrimidine 4.7 g (0.278 mol) of gaseous ammonia were passed over the course of 1 hour into a stirred mixture of 38.0 g (0.147 mol) of 2-fluoro(chloro)-4-trifluoromethoxy-6-trifluoromethylpyrimidine and 150 ml of diethyl ether at −75° to −70° C. The mixture was stirred for 2 hours each at −75° and at 25° C. The precipitate was filtered off with suction, and the organic phase was extracted 3x with water, dried and evaporated. Chromatography on silica gel with methyl tert.-butyl ether yielded 20.4 g (56.1% of theory) of the title compound of melting point 47°-49° C.

III CONVERSION OF PYRIMIDINES I INTO HERBICIDAL SULFONYLUREAS

Examples III.1 to III.8

Example III.1

2-Amino-4-methoxy-6-trifluoromethoxypyrimidine 2.7 g (0.015 mol) of 30% strength sodium methylate were added over the course of 15 minutes to 2.95 g (0.015 mol) of 2-amino-4-fluoro-6-trifluoromethoxypyrimidine in 50 ml of methanol while stirring at −5° to 0° C. The reaction mixture was stirred at 0° C for 1 hour, warmed to 25° C. and then concentrated under reduced pressure, stirred with water and extracted 2× with methylene chloride. Drying and concentrating under reduced pressure resulted in 3.1 g (98% of theory) of the title compound of $n_D^{25}=1.4770$.

Example III.2

2-Amino-4-chlorodifluoromethoxy-6-methoxypyrimidine 26. 1 g (0. 145 mol) of 30% strength sodium methylate were added over the course of 15 minutes to 31.0 g (0.145 mol) of 2-amino-4-chlorodifluoromethoxy-6-fluoropyrimidine in 300 ml of methanol while stirring at −10° to 0° C. The reaction mixture was stirred at 0° C. for 30 minutes and at 25° C. for 1 hour and then concentrated under reduced pressure and worked up as above. 31.6 g (96.6% of theory) of the title compound were obtained as a colorless oil with $n_D^{22}=1.5039$.

Example III.3

4-Chlorodifluoromethoxy-2-methylamino-6-methoxypyrimidine 4.7 g (0.026 mol) of 30% strength sodium methylate were added over the course of 10 minutes to 6.0 g (0.0263 mol) of 4-chlorodifluoromethoxy-6-fluoro-2-methylaminopyrimidine in 100 ml of methanol while stirring at 0° C. The mixture was stirred at 0° C. and at 25° C. for 1 hour each and worked up as usual, resulting in 6.3 g (100% of theory) of the title compound of melting point 49°-53° C.

Example III.4

4-Chlorodifluoromethoxy-6-dimethylamino-2-methylaminopyrimidine 1.9 g (0.0417 mol) of gaseous dimethylamine were passed over the course of 10 minutes into a stirred mixture of 8.9 g (0.0417 mol) of 2-amino-4-chlorodifluoromethoxy-6-fluoropyrimidine and 100 ml of tetrahydrofuran at 0° C. The mixture was stirred at 0° C. for 1 hour and at 25° C. for 2 hours and worked up as usual, resulting in 9.7 g (97.5% of theory) of the title compound of melting point 127°-130° C.

Example III.5

Methyl 2-(4-fluoro-6-trifluoromethoxy-2-pyrimidinylaminocarbonylaminosulfonyl)benzoate 3.6 g (0.015 mol) of 2-methoxycarbonylbenzenesulfonyl isocyanate in 15 ml of 1,2-dichloroethane were added over the course of 15 minutes to a stirred mixture of 2.95 g (0.015 mol) of 2-amino-4-fluoro-6-trifluoromethoxypyrimidine and 100 ml of 1,2-dichloroethane at 25° C., and the mixture was stirred at 25° C. for 12 hours. The solution was concentrated under reduced pressure, and the residue was stirred with 1:1 ether/petroleum ether. Filtration with suction and drying yielded 4.8 g (73.3% of theory) of the title compound of melting point 157°-161° C.

Example III.6

Ethyl 2-(4-chloro-6-trifluoromethoxy-2-pyrimidinylaminocarbonylaminosulfonyl)benzoate 2.55 g (0.01 mol) of 2-ethoxycarbonylbenzene isocyanate in 10 ml of methylene chloride were added over the course of 10 minutes to a stirred mixture of 2.1 g (0.01 mol) of 2-amino-4-chloro-6-trifluoromethoxypyrimidine and 100 ml of methylene chloride at 25° C. The mixture was stirred at 25° C. for 12 hours and filtered with suction to remove a few insolubles. Concentration of the filtrate under reduced pressure, stirring of the residue with 1:1 ether/petroleum ether, filtration with suction and drying yielded 4.0 g (85.4% of theory) of the title compound of melting point 148°-151° C.

Example III.7

Methyl 2-(4-methoxy-6-trifluoromethoxy-2-pyrimidinylaminocarbonylaminosulfonyl)benzoate 4.8 g (0.02 mol) of 2-methoxycarbonylbenzenesulfonyl isocyanate in 10 ml of acetonitrile were added over the course of 15 minutes to a stirred mixture of 4.1 g (0.02 mol) of 2-amino-4-methoxy-6-trifluoromethoxypyrimidine and 100 ml of acetonitrile at 25° C., and the mixture was then stirred for 12 hours. The precipitate was removed (2.4 g of melting point 141°-143° C.) and then the filtrate was concentrated under reduced pressure and stirred with ether/petroleum ether, and the solid was filtered off with suction and dried. A further 4.3 g of the title compound of melting point 141°-143° C. were obtained. The total yield was 6.7 g (74.4% of theory).

Example III.8

Sodium salt of methyl 2-(4-methoxy-6-trifluoromethoxy-2-pyrimidinylaminocarbonylaminosulfonyl)benzoate 2.4 g (0.053 mol) of methyl 2-(4-methoxy-6-trifluoromethoxy-2-pyrimidinylaminocarbonylaminosulfonyl)benzoate (active substance example 5.001) were dissolved in 50 ml of methanol and,, at 25° C., 1.0 g (0.053 mol) of 30% strength sodium methylate solution in methanol was added, and the mixture was stirred for 10 minutes. Removal of the solvent by distillation under reduced pressure yielded 2.5 g (100% of theory) of the title compound of melting point 175° C.

I claim:

1. A substituted 2-amino(fluoroalkoxy)pyrimidine of the formula I

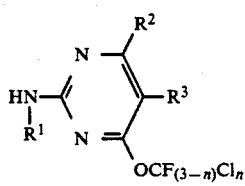

where $R^1$ is hydrogen, $C_1$–$C_4$-alkyl, $C_3$–$C_4$-alkenyl or $C_3$–$C_4$-alkynyl, $R^2$ is hydrogen, halogen, $C_1$–$C_4$-haloalkyl, trifluoromethoxy or chlorodifluoromethoxy, $R^3$ is hydrogen, halogen or $C_1$–$C_4$-haloalkyl and n is 1.

2. A process for preparing a 2-amino(fluoroalkoxy)pyrimidine of the formula I

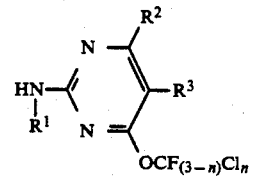

where $R^1$ is hydrogen, $C_1$–$C_4$-alkyl, $C_3$–$C_4$-alkenyl or $C_1$–$C_4$-alkynyl, $R^2$ is hydrogen, halogen, $C_1$–$C_4$-haloalkyl, trifluoromethoxy or chlorodifluoromethoxy, $R^3$ is hydrogen, halogen or $C_1$–$C_4$-haloalkyl and n is 0 or 1, which comprises reacting a 2-halopyrimidine of the formula II

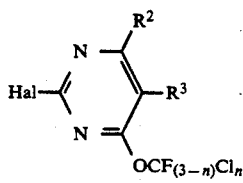

where Hal is fluorine, chlorine, bromine or iodine, and $R^2$, $R^3$ and n have the abovementioned meanings, with an amine of the formula III

where $R^1$ has the abovementioned meaning, in the presence or absence of an organic base.

3. The process of claim 2, wherein the amine III is ammonia.

4. The process of claim 2, wherein the amine III is methylamine.

5. The process of claim 2, wherein the reaction is carried out at from −80° to 40° C.

6. 2-Amino-4-chlorodifluoromethoxy-6-fluoropyrimidine.

7. 2-Amino-4-chloro-6-chlorodifluoromethoxypyrimidine.

* * * * *

UNITED STATES PATENT AND TRADEMARK OFFICE
CERTIFICATE OF CORRECTION

PATENT NO. : 5,283,332
DATED : February 1, 1994
INVENTOR(S) : Gerhard HAMPRECHT

It is certified that error appears in the above-identified patent and that said Letters Patent is hereby corrected as shown below:

ON THE TITLE PAGE, ITEM [30]:

Insert the following:

--Foreign Application Priority Data
  March 8, 1990 [DE] Fed. Rep. of Germany 4007316--.

IN THE CLAIMS

Claim 2, column 14, line 12, "$C_1-C_4$-alkynyl" should read --$C_3-C_4$-alkynyl--.

Signed and Sealed this

Fourth Day of April, 1995

Attest:

BRUCE LEHMAN

Attesting Officer

Commissioner of Patents and Trademarks